US010433757B2

(12) United States Patent
Chen

(10) Patent No.: US 10,433,757 B2
(45) Date of Patent: Oct. 8, 2019

(54) DIAGNOSTIC METHOD AND APPARATUS FOR BRAIN INJURY BASED ON EMG FREQUENCY POWER SPECTRA ANALYSIS

(71) Applicant: Jian Chen, Sudbury (CA)

(72) Inventor: Jian Chen, Sudbury (CA)

( * ) Notice: Subject to any disclaimer, the term of this patent is extended or adjusted under 35 U.S.C. 154(b) by 154 days.

(21) Appl. No.: 15/526,025

(22) PCT Filed: Dec. 29, 2015

(86) PCT No.: PCT/CA2015/051377
§ 371 (c)(1),
(2) Date: May 11, 2017

(87) PCT Pub. No.: WO2016/123689
PCT Pub. Date: Aug. 11, 2016

(65) Prior Publication Data
US 2018/0049662 A1 Feb. 22, 2018

(30) Foreign Application Priority Data
Feb. 2, 2015 (CA) .................................. 2880623

(51) Int. Cl.
*A61B 5/0488* (2006.01)
*A61B 5/11* (2006.01)
*A61B 5/00* (2006.01)

(52) U.S. Cl.
CPC ............ *A61B 5/0488* (2013.01); *A61B 5/112* (2013.01); *A61B 5/4064* (2013.01); *A61B 5/4076* (2013.01)

(58) Field of Classification Search
USPC ....................................................... 600/543
See application file for complete search history.

(56) References Cited

U.S. PATENT DOCUMENTS 6,416,480 B1 * 7/2002 Nenov ................. A61B 5/1106
600/557
6,571,193 B1    5/2003 Unuma et al.
(Continued)

FOREIGN PATENT DOCUMENTS

CA      2880623 A1    8/2016
WO  2016123689 A1    8/2016

OTHER PUBLICATIONS

Hutchison W. D. et al. Neuronal Oscillations in the Basal Ganglia and Movement Disorders: Evidence from Whole Animal and Human Recordings. The Journal of Neuroscience, 2004; 24(42):9240-9243) (Year: 2004).*

(Continued)

*Primary Examiner* — Christian Jang
*Assistant Examiner* — Mitchell E Alter
(74) *Attorney, Agent, or Firm* — Bereskin & Parr LLP/S.E.N.C.R.L., s.r.l.; Tony Orsi; Ahmed Elmallah

(57) ABSTRACT

A method and a device for diagnosing brain injury (e.g. concussion) based on analysis of electromyogram (EMG) signals and presence of neurological modulation impairment of motor activity are described. The method consists of recording specific EMG signals under defined conditions, processing the acquired EMG signals, extracting the relevant information, and making diagnosis of brain injury and disorders that are associated with brain pathology. Specifically, the steps and device involved in the method include placing an EMG electrode set on the subject's body area, acquiring EMG signals from a subject's muscle(s) undergoing contraction, processing the acquired EMG signals using a signal processing algorithm that includes Fourier transformation. The resulting EMG data with a frequency domain (frequency power spectra) are then analyzed in comparison with databases stored in the device and used to determine anomaly of diagnostic value in the EMG power (Continued)

spectra from subjects. A diagnosis can be made based the altered EMG frequency power spectra that reflect the neurological modulation impairment of motor neurons. The diagnostic value, determination, management suggestions are displayed on the device.

26 Claims, 4 Drawing Sheets

(56) References Cited

U.S. PATENT DOCUMENTS

| | | | | |
|---|---|---|---|---|
| 2002/0193670 | A1* | 12/2002 | Garfield | A61B 5/0444 600/304 |
| 2005/0273017 | A1* | 12/2005 | Gordon | A61B 5/048 600/544 |
| 2011/0144520 | A1* | 6/2011 | Causevic | A61B 5/0476 600/544 |
| 2011/0208444 | A1* | 8/2011 | Solinsky | A61B 5/112 702/41 |
| 2012/0108999 | A1* | 5/2012 | Leininger | A61B 5/0004 600/546 |
| 2013/0012830 | A1 | 1/2013 | Leininger et al. | |
| 2018/0014784 | A1* | 1/2018 | Heeger | A61B 5/0006 |

OTHER PUBLICATIONS

Lambertsen, Nicholas. "Non-Linear Dynamical Analysis of a Visual-Motor Tracking Task for Baseline Testing and Post-Concussion Evaluation of Intercollegiate Athletes." (2015) (Year: 2015).*
International Search Report and Written Opinion dated Mar. 2, 2016 in corresponding International Patent Application No. PCT/CA2015/051377.
Albers, et al., "At the interface of sensory and motor dysfunctions and Alzheimer's Disease", Alzheimers Dement., 2015, 11(1): 70-98.
Buchman, et al., "Loss of motor function in preclinical Alzheimer's disease", Expert Rev Neurother., 2011; 11(5): 665-676.
Hutchison, et al., "Neuronal Oscillations in the Basal Ganglia and Movement Disorders: Evidence from Whole Animal and Human Recordings", The Journal of Neuroscience, 2004; 24(42):9240-9243.
Brown, "Oscillatory Nature of Human Basal Ganglia Activity: Relationship to the Pathophysiology of Parkinson's Disease", Movement Disorders, 2003; 18(4):357-363.
Brown, et al., "What do the basal ganglia do?", Lancet, 1998; 351:1801-1804.
Hassler, "Brain mechanisms of intention and attention with introductory remarks on other volitional processes", Prog Brain Res, 1980; 54:585-614.
Brown, "Cortical drives to human muscle: the Piper and related rhythms", Prog Neurobiol., 2000, 60(1):97-108.
Sailer, et al., "Subthalamic nucleus stimulation modulates afferent inhibition in Parkinson disease", Neurology, 2007; 68:356-363.
Wagle Shukla, et al. "Long-term subthalamic nucleus stimulation improves sensorimotor integration and proprioception", J Neurol Neurosung Psychiatry, 2013; 84:1020-1028.
Williams, et al., "Dopamine-dependent changes in the functional connectivity between basal ganglia and cerebral cortex in humans", Brain, 2002; 125(Pt 7):1558-1569.
Dieckmann, "Cortical synchronised and desynchronised responses evoked by stimulation of the putamen and pallidum in cats", J Neurol Sci., 1968; 7(2):385-391.
Hassler, et al., "Arrest reaction, delayed inhibition and unusual gaze behaviour resulting from stimulation of the putamen in awake unrestrained cats", Brain Res., 1967; 5(4):504-508.
McKee, et al., "The spectrum of disease in chronic traumatic encephalopathy", Brain, 2013; 136(Pt 1): 43-64.
Buracchio, et al., "The trajectory of gait speed preceding mild cognitive impairment", Arch. Neurol., 2010; 67(8):980-986.
Camicioli, et al., "Motor slowing precedes cognitive impairment in the oldest old", Neurology, 1998; 50(5):1496-1498.
Portet, et al., "Extrapyramidal signs before and after diagnosis of incident Alzheimer disease in a prospective population study", Arch. Neurol., 2009; 66(9):1120-1126.
Wilson, et al., "Parkinsonianlike signs and risk of incident Alzheimer disease in older persons", Arch. Neurol., 2003; 60(4):539-544.
Nuwer, et al., "Routine and quantitative EEG in mild traumatic brain injury", Clinical Neurophysiology, 2005, 116(9): 2001-2025.
Packard, et al. "Learning and memory functions of the basal ganglia", Annual review of neuroscience, 2002, 25(1): 563-593.
Levy, et al., "Apathy and the functional anatomy of the prefrontal cortex-basal ganglia circuits", Cerebral cortex, 2006, 16(7): 916-928.
Middleton, et al., "Basal ganglia and cerebellar loops: motor and cognitive circuits", Brain research reviews, 2000, 31(2-3): 236-250.
Leisman, et al., "Cognitive-motor interactions of the basal ganglia in development", Frontiers in Systems Neuroscience, 2014, 8(16): 1-18.
Concussion in Sport Group, "SCAT3—Sport Conccussion Assessment Tool—3rd Edition", British Journal of Sports Medicine, 2013, 47(5): 259-262.

* cited by examiner

DIAGNOSTIC METHOD AND APPARATUS FOR BRAIN INJURY BASED ON EMG FREQUENCY POWER SPECTRA ANALYSIS

CROSS-REFERENCE TO RELATED APPLICATIONS

This patent application claims priority under paragraph 28.1(1)(a) of the Patent Act on Patent Application No(s). 2,880,623 filed in Canada Feb. 2, 2015, the entire contents of which are hereby incorporated by reference.

FIELD OF THE INVENTION

The present disclosure relates to the field of neurological assessment and, in particular, a method and an apparatus for determining brain injuries by recording electromyogram (EMG), transforming the acquired EMG signals into frequency power spectrum, and detecting anomaly in specific ranges of the spectrum that are signature(s) of or associated with traumatic brain injuries and degenerative brain diseases.

BACKGROUND OF THE INVENTION

Current diagnostic brain imaging devices such as CT, MRI, PET scan, and fMRI can be useful in detecting anomaly in patients with traumatic brain injuries. However, most cases of the brain trauma produce mild traumatic brain injuries (mTBI) such as a concussion. These conditions are not detectable with routine diagnostic brain imaging devices. For example, diffuse axonal injury is one of the most prevalent damage in mTBI. Yet, most clinical imaging techniques cannot capture diffuse pathological axonal injuries. In cases of brain trauma that produced significant focal brain damages visible on diagnostic images, the symptoms, sequelae, recovery, and long term outcomes often do not correlate with the severity of brain damage as defined by the imaging techniques, indicating other factors may have greater bearing on symptomology and brain pathology. Indeed, brain cadaver studies have revealed common and extensive axonal disruption, perivascular astrocyte tangles, and neurofibrillary tangles in brains with concussion history and chronic symptoms. Evidence from in vivo studies also show that the extent of white matter abnormalities after mTBI correlates with the severity of post-concussion cognitive problems.

The prevalence of mTBI and sometime devastating long term consequence of concussions illustrate the needs for more sensitive and objective tests. In Canada, the yearly incidents of concussion are estimated to be 160,000 cases while in USA the annual incidents of mTBI approach one million. mTBI impacts diverse brain functions that include cognition, emotion, motor control, sensation, and neuro-behaviors. Although repertoire and severity of concussion effects varies, the sequalae of concussion can be debilitative particularly among at risk groups such as younger individuals, athletes, and military personnel.

mTBI also increase risks to developing dementia, early senility, Parkinson's disease, and Alzheimer's disease. Although underlining etiology and pathology differ, these diseases or disorders share motor dysfunctions and cognitive impairment with mTBI. Several studies have demonstrated that a more rapid rate of motor decline in cognitively intact individuals predicted the subsequent development of mild cognitive impairment and Alzheimer's disease, and loss of motor function can precede cognitive impairment (see Aron S Buchman and David A Bennett. Loss of motor function in preclinical Alzheimer's disease. Expert Rev Neurother. 2011 May; 11(5): 665-676).

Repetitive brain trauma may also lead to chronic traumatic encephalopathy, a progressive neurodegenerative disease that expresses a wide range of symptoms including motor deficits, cognitive impairment, depression, and violent mood alteration. According to autopsy studies on brains of deceased former National Football League players, 95% of those brains had chronic traumatic encephalopathy that is marked by wide-spread neurofibrillary tangles and perivascular astrocyte tangles as well as significant deposits of neurodegenerative biomarkers. However, currently, the condition of chronic traumatic encephalopathy can only be diagnosed by post-mortem autopsy.

One of challenges in mTBI diagnosis, prognosis, and management is the lack of a practical and objective diagnostic test. Currently, a concussion may be recognized based on observation and assessment of overt signs and symptoms. However, there remain the needs for improvements on many clinical related issues such as under-diagnosis of concussion, identification of impaired functional regions of the brain, determinations of severity and recovery progress, and correlation of brain injury with symptomology. Furthermore, a lack of objective and sensitive test for brain injury leads to repetitive injuries in athletes and increases the risk for developing long-term effects of brain injury such as chronic traumatic encephalopathy and other neurodegenerative diseases. The development of a sensitive test for mTBI may provide a useful tool that will help to solve some of these clinical dilemmas.

It is the object of the present invention to address the deficiencies of the prior art. The principle and strategy deployed in this invention to provide the mTBI diagnosis have not be applied or reported before.

SUMMARY OF THE INVENTION

This disclosure contains several aspects of the invention that are designed to enable the collection of EMG signals under defined conditions in which extensive neurological modulations are at work from various brain regions and functional systems, extraction of the relevant information from the recorded EMG signals, diagnosis of TBI and disorders that are associated with brain pathology, and display of diagnostic values, results, and management information for the patient.

An object of the present invention is to provide a method and a device that will detect anomaly in EMG power spectra of a subject comprising the steps: acquiring EMG signal from muscle activities; transforming the recorded EMG into power spectra; extracting qualitative features in the said spectra; comparing the quantitative features of the said spectra against a databank of normative and abnormal comparison data; diagnosing the presence of anomaly in the subject's power spectra that are associated with brain injuries resulting from trauma or diseases.

In an exemplary embodiment of this invention, EMG signals are acquired from muscles performing tasks that elicit plurality of influence from neurological systems and regions of the brain. The exemplary tasks include walking gait cycle and balance performance of a subject. The neurological systems and brain regions that are important for balance include but limited to cortical areas, basal ganglia, cerebelli, vision, vestibular system, and proprioceptive feedback mechanism. These influences contribute to the neurological modulation of motor activities imbedded in the acquired EMG signals. In accordance to this invention, a method and an apparatus are described in order to process and analysis the acquired EMG signals. The invention further includes extraction of qualitative features from the processed EMG signals and detection of anomaly of neurological modulation that are associated with brain injuries and neurodegenerative diseases.

In an exemplary embodiment of this invention, the acquired EMG signal is transformed into frequency power spectra with Fourier transformation algorithm. Algorithmic operations are executed by a processor and specified by software stored in a memory unit. In accordance with this invention, the power spectra is further analysed to extract quantified features and to build classifier for the purpose of diagnosis and classification of impairment of neurological modulation of motor activities.

In accordance with this invention, the base unit contains in its memory databank of comparison data. The databank includes normative data of subjects with similar age and without brain injury and disease. The databank further includes data of subjects with brain injury and neurodegenerative diseases. In accordance with the method, a subject's power spectra are compared against the databank in order to make determination of the subject's status of neurological modulation of motor activity and diagnosis of brain injury or disease.

Consistent with the current invention, there is an apparatus provided for assessment of neurological modulation of motor activity of a subject comprising an EMG sensor device and a portable base unit operatively connected to the EMG sensor. The base unit comprises an analog electronic block as an EMG amplifier, a memory with installed software and databank, an interactive screen, and a processor configured to perform algorithm. The apparatus is designed to provide diagnosis of brain injury and disease based on the assessment of neurological modulation of motor activity through the EMG frequency power spectra analysis.

DETAILED DESCRIPTION

A method and a device 100 for diagnosing brain injury (e.g. concussion) based on impairment of neurological modulation of motor neuron activity according to analysis of EMG power spectra are described. Exemplary embodiments consistent with the current invention will be described with the aid of Figs and flowchart that depict components and steps that are identified with reference numbers. The exemplary embodiments of the method will be disclosed first concerning steps and physiological base of neurological modulation impairment of motor activity; the exemplary embodiments of device will be described in the latter portion of this disclosure.

Figure 1:
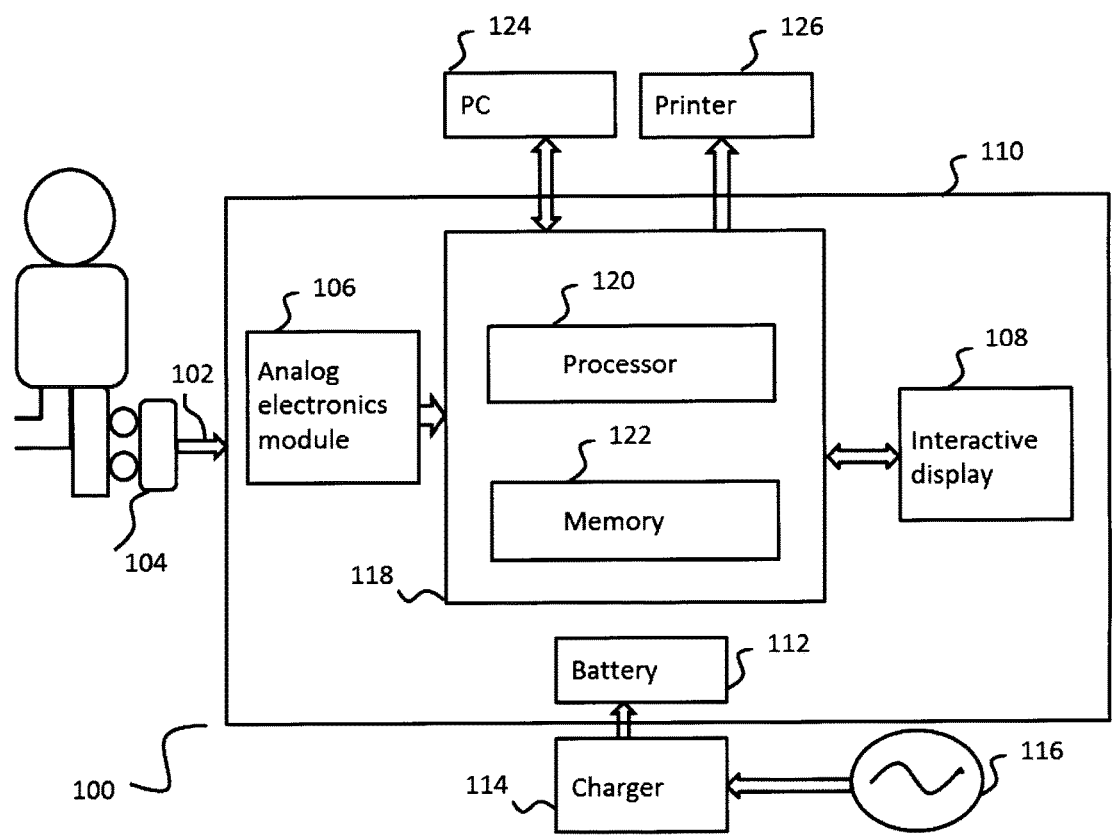
FIG. 1 is a schematic of a device for the assessment of neurological modulation impairment of motor control and providing diagnosis of mTBI and neurodegenerative diseases, in accordance with the present invention.
Figure 2:
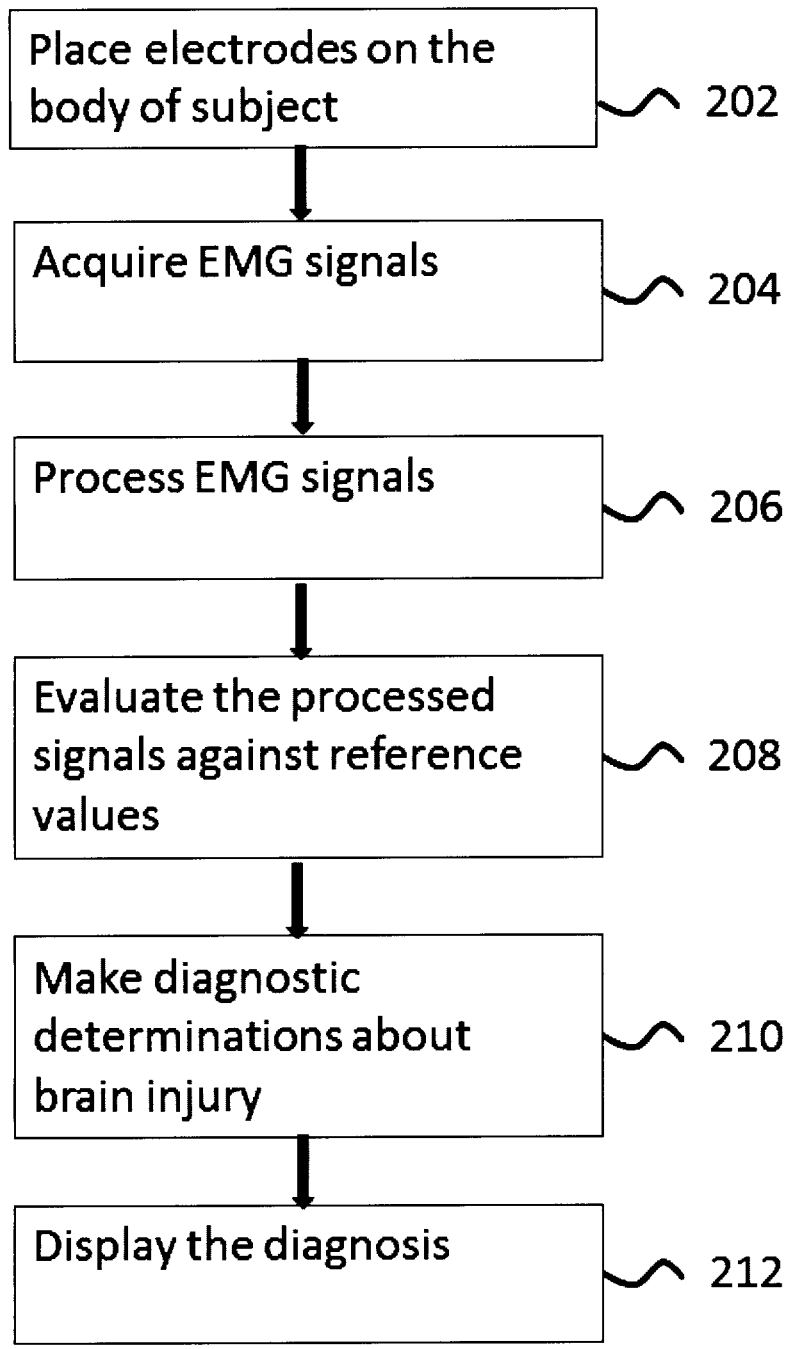
FIG. 2 is a flowchart indicating steps that leads to diagnostic determination and display of results, in accordance with the present invention.

FIG. 1 is a schematic of a device for the assessment of neurological modulation impairment of motor control and providing diagnosis of mTBI, chronic traumatic encephalopathy, and other neurodegenerative diseases associated with long-term effects of traumatic brain injuries, in accordance with the present invention. FIG. 2 is a flowchart indicating steps that leads to diagnostic determination and display of results, in accordance with the present invention.

The method consists of collecting specific EMG signal under defined conditions (steps of 202 and 204), processing and transforming the acquired EMG signals into EMG power spectra (step of 206), extracting quantitative features from the transformed EMG, and comparing (step of 208) the subject's EMG power spectra and quantitative features against those in a database to determine if the subject has abnormality and impairment in neurological modulation of motor activities (step 210) that are associated with brain injury, chronic traumatic encephalopathy, and neurodegenerative diseases. Specifically, the steps and device involved in the method include placing an EMG sensor device 104 on the subject's body area (step of 202), acquiring EMG signals from a subject's muscle(s) (step of 204), processing the acquired EMG signals using a signal processing algorithm that includes Fourier transformation (step of 206). The resultant EMG data with energy distribution over a frequency domain (frequency power spectra) is then analyzed (step of 208) in comparison with data bases stored in the device's memory 122 and used to determine anomaly of diagnostic value in the EMG power spectra that reflect impaired neurological modulation of motor neurons associated with brain injury, chronic traumatic encephalopathy, and neurodegenerative diseases (step of 210). The diagnostic value and patient management suggestions are displayed (step of 212) on the interactive screen 108.

Consistent with the method in this invention, the step of extracting quantitative features from the power spectra include performing algorithm of the software in the memory 122 by the processor 120 in the base unit 100 to obtain linear and non-linear quantitative features from the EMG power spectra. In an exemplary embodiment of this invention, quantitative features computed include, but are not limited to, total power in the entire frequency range, relative power for each frequency, average and mean power in different frequency bandwidths, ratios of powers in one bandwidth over another bandwidth, statistical harmonics variables, Wavelet features, fractal dimension, coherence, and symmetry.

Further detailed description will be made on the preferred embodiments consistent with this invention. Whenever possible, reference on elements of this disclosure will be accompanied with drawings that depict elements and steps. It should be understood that this disclosure is not limited to the described embodiments. Any modification or variations that are within the spirit and scope of this invention should be considered consistent with the current invention as defined by the claims and equivalents thereto.

In accordance with this invention, the method requires placing electrodes (step of 202) of an EMG sensor device 104 to record EMG signals (step of 204) of active muscles under conditions whereby multiple neurological inputs and feedback loops are actively engaged in modulating the activities of motor neurons that innervate the muscles. In an exemplary embodiment, conditions that engage multiple neurological inputs include balance performance of a subject. The neurological systems and brain regions that are important for balance include but limited to cortical areas, basal ganglia, cerebelli, vision, vestibular system, and proprioceptive feedback mechanism. Brain injuries and neurological diseases can distort EMG signals. After transforming the acquired EMG signals (step of 206) into EMG power spectra, a plethora of quantitative features can be calculated and used to distinguish abnormal EMG from normal EMG. Different brain pathology and dysfunction may affect differently signal strength in particular bandwidth(s) of EMG power spectra, therefore, analysis of EMG power spectra can reveal EMG anomaly particular to the dysfunction of a brain region or a functional network and provide bases for diagnosis in accordance with the current invention.

The method of assessing neurological modulation of motor activity using recorded EMG according to the invention may provide that acquiring EMG signal (step of 204) from muscles include muscle(s) undergoing contraction of different types and intensities while performing certain tasks such as walking gait cycle and balancing. The step of acquiring EMG signal according to the invention may include recording EMG signals from muscles engaged in controlling joint movement and body posture during a variety of balance tests such as single-limb stance and two legged stance on flat, tilted, and uneven surfaces while the eyes are open and or eyes closed. Acquiring EMG signals according to the invention may further include placing electrode(s) and recording EMG over the skin area under which peroneus longus muscle lies and is actively engaged in ankle control while the subject is maintaining one legged standing. Acquiring EMG signal according to the invention may include recording EMG of muscles of the lower extremity such as peroneus brevis, tibialis anterior, soleus, and gastrocnemius, gluteal muscles, hip flexors and extensor, and knee extensor muscles during balance tests. According to the invention, acquiring EMG signals may include recording EMG from muscles of both limbs during balance tests.

Consistent with the method in this invention, the step of transforming (step of 206) EMG signals into frequency power spectra may include Fourier transformations such as fast Fourier transformation (FFT) and discrete Fourier transformation (DFT). Transforming EMG signal according to the invention may include wavelet transformation. According to the invention, transforming EMG signals may include obtaining power spectra with the frequency spread or range up to 500 Hz or greater.

In an exemplary embodiment, EMG power spectra of subjects are assessed (step of 208) with reference to a databank of comparison data. The databank includes a normative data indicative of normal power spectra that are used to derive quantitative features distinguishing the normative EMG signals from those associated with brain injury and disorder. In accordance with this invention, the quantitative features include energy or signal strength in regions of high gamma frequency (>70 Hz). In accordance with the current invention, the method of assessing neurological modulation of motor activity and providing diagnosis of brain injury has been applied to 118 subjects with (n=40) and without mTBI (n=78). The diagnosis for brain injury has high sensitivity (low false negative rate) and specificity (false negative rate).

Figure 3:
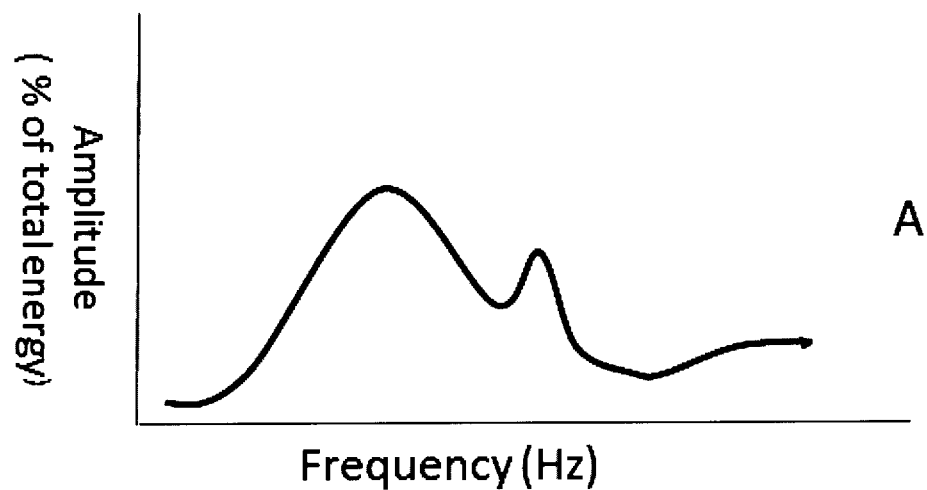
FIG. 3 illustrates an exemplary normal (A) and an impaired (B) EMG frequency power spectra.
Figure 3:
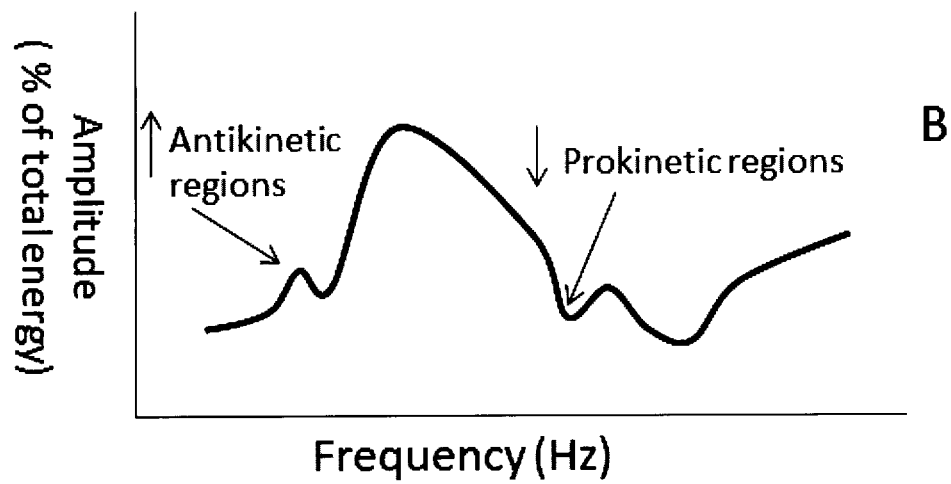
Figure 4:
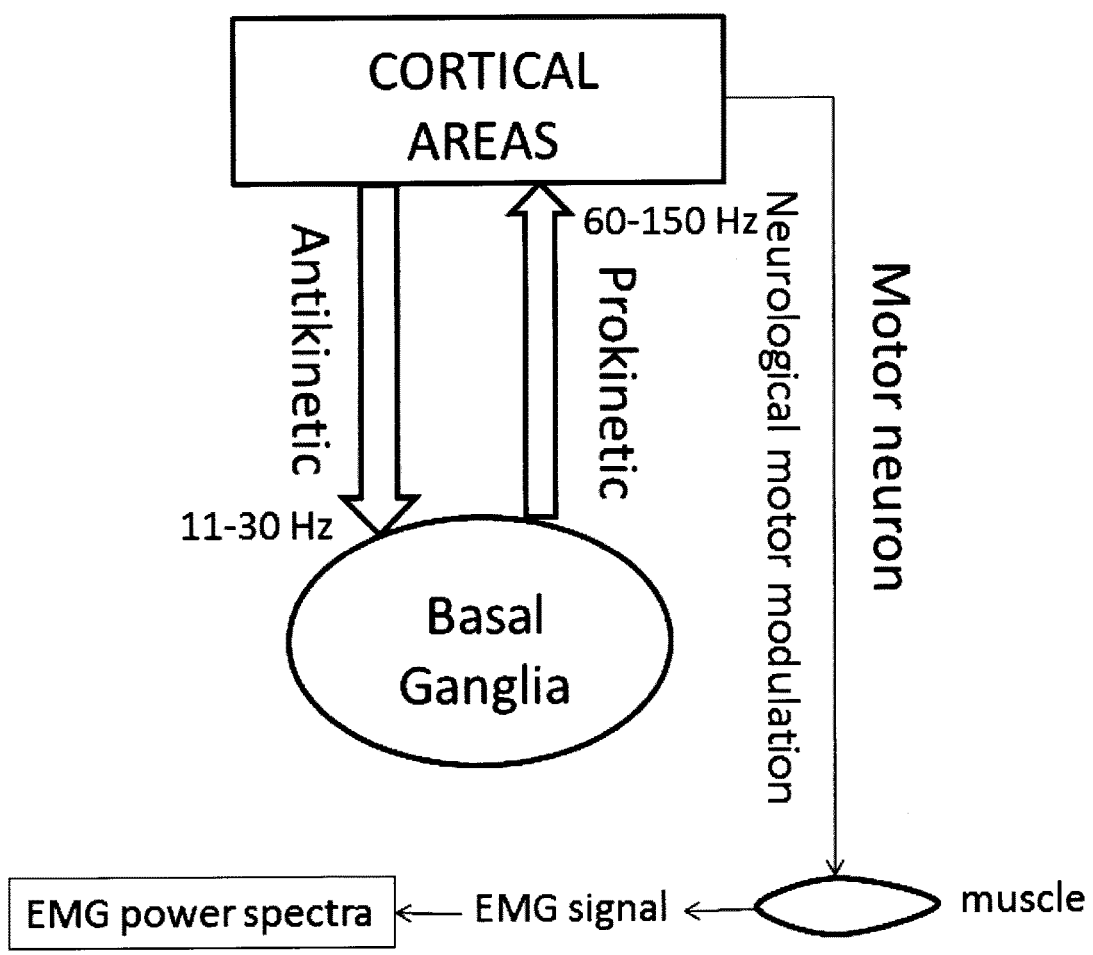
FIG. 4 illustrates an exemplary and simplified oscillation model of neurological modulation of motor-neuron activity.

In accordance with the current invention, quantitative features and their functional importance are disclosed in reference to the analysis of the EMG power spectra. FIG. 3 illustrates an exemplary normal (A) and impaired (B) EMG power spectra. FIG. 4 illustrates an exemplary and simplified oscillation model of neurological modulation of motorneuron activity. In an exemplary embodiment of the method, the quantitative features derived from the power spectra include averaged energy within bandwidths centered on 30 Hz, 35-70 Hz, 74-75 Hz, 79-80 Hz, 93-95 Hz, and 160-320 Hz. In accordance with this invention, comparing (step of 208) quantitative features of the subject's EMG against those in a normative database include determination of energy differences in and around 30 Hz, 35-70 Hz, 74-75 Hz, 79-80 Hz, 93-95 Hz, and 160-320 Hz that are expected to be different in subjects with brain injury and neurodegenerative diseases in comparison with similar subjects without brain injury or neurodegenerative diseases.

In an exemplary embodiment of this invention, the anomaly of EMG power spectra associated with subjects with mTBI include the significantly reduced signal strength or energy within bandwidths centered on 74-75 Hz, 79-80 Hz, and 93-95 Hz. In accordance with the current invention, the disclosure of these depressed bandwidths represents a novel and significant discovery. There have been no speculations and reports in the literature on the existence of these multiple discrete bandwidths in the region viewed as prokinetic in basal ganglia (see Hutchison W. D. et al. Neuronal Oscillations in the Basal Ganglia and Movement Disorders: Evidence from Whole Animal and Human Recordings. The Journal of Neuroscience, 2004; 24(42):9240-9243). The mTBI-induced depression of regions within the high gamma frequency range suggests the functional importance of the prokinetic frequency oscillations (>70 Hz) in motor cortex and basal ganglia (see Brown P. Oscillatory Nature of Human Basal Ganglia Activity: Relationship to the Pathophysiology of Parkinson's Disease Movement Disorders. 2003; 18(4):357-363). Prokinetic oscillations do not initiate movement and is modulatory in its nature that enhances cortico-cortical communication (see Brown P, Marsden C D. What do the basal ganglia do? Lancet 1998; 351:1801-1804.). The high gamma oscillation serves to bind different areas of cortical activities to enhance communication among cortical areas and can result in swift executive motor output and coordinated motor modulation (see Hassler R. Brain mechanisms of intention and attention with introductory remarks on other volitional processes. Prog Brain Res 1980; 54:585-614; Brown P. The Piper rhythm and related activities in man. Prog Neurobiol 1999; 60:97-108.). Both Subthalamic deep brain stimulation (STN-DBS) at 60-100 Hz and dopaminergic prodrug of Levodopa increase the intensity of oscillations in motor cortex at frequencies greater than 60 Hz in Parkinsonian patient resulting in significant clinical improvement of movement disorders. The precise frequency bandwidths that are enhanced depend on the experimental conditions and recording techniques involved. The prokinetic effect of high gamma frequency may also include its ability to partially overcome the impaired sensorimotor integration seen in Parkinson's disease. STN-DBS improves sensorimotor integration by ameliorating short-latency afferent inhibition and restoring the long-latency afferent inhibition (see Sailer A, Cunic D I, Paradiso G O, et al. Subthalamic nucleus stimulation modulates afferent inhibition in Parkinson disease. Neurology 2007; 68:356-363; Wagle Shukla A, Moro E, Gunraj C, et al. Long-term subthalamic nucleus stimulation improves sensorimotor integration and proprioception. J Neurol Neurosurg Psychiatry 2013; 84:1020-1028.).

In the method accordance with the current invention, quantitative features derived from the EMG power spectra analysis include increased signal strength or energy in the discrete bandwidths centered around 30 Hz, 160-320 Hz, and >320 Hz in subjects with mTBI. These changes in EMG power spectra are disclosed as a novel discovery for the first time in accordance with the current invention. The increased energy of oscillation at around 30 Hz may contribute to the impaired motor modulation and movement seen in subjects with brain injury. In patients with Parkinsonian disorder, basal ganglia exhibit increased activity at 11 to 30 Hz (see Williams D, Tijssen M, van Bruggen G, Bosch A, Insola A, Di Lazzaro V, Mazzone P, Oliviero A, Quartarone A, Speelman H, Brown P. Dopamine dependent changes in the functional connectivity between basal ganglia and cerebral cortex in the human. Brain 2002; 125:1558-1569). This increase is considered anti-kinetic and is associated with akinesia and dyskinesia. Consistent with such an anti-kinetic effect is the observation that stimulation of the feline pallidum and entopeduncular nucleus at around 30 Hz leads to freezing of movement (see Dieckmann G. Cortical synchronised and desynchronised responses evoked by stimulation of the putamen in cats. J Neurol Sci 1968; 7:385-310; Hassler R, Dieckmann G. Arrest reaction, delayed inhibition and unusual gaze behaviour resulting from stimulation of the putamen in awake unrestrained cats. Brain Res 1967; 5:504-508).

In the method consistent with this invention, making diagnosis (step of 210) of brain injury and neurodegenerative diseases includes determining abnormal neurological modulation of motor activity reflected in EMG power spectra of the subject consisting of reduced signal strength or energy in discrete bandwidths in the range of high gamma frequency of the power spectra. Depressed signal regions within high gamma frequency, including 74-75 Hz, 79-80 Hz, and 93-95 Hz, are associated with brain injury and neurodegenerative diseases such as chronic traumatic encephalopathy, Alzheimer disease and Parkinson's disease in accordance with this invention. The diffused damages to neurons and axonal connection in the brain are shared in patients with mTBI, Alzheimer disease, and Parkinson's disease. Concussion increases the risks of developing both Alzheimer disease and Parkinson's disease (see McKee A. C. et al. The spectrum of disease in chronic traumatic encephalopathy. Brain 2013; 136: 43-64). Altered neurological motor modulation in EMG reflects the dysfunction and comprised integrity of widely distributed cortical and subcortical motor-related brain regions, as well as sensory, visuospatial and cognitive functions. Consistent with the method, neurological modulation impairment includes Alzheimer disease. Motor disorder can precede clinical symptoms of Alzheimer disease by several years (see Aron S Buchman and David A Bennett. Loss of motor function in preclinical Alzheimer's disease. Expert Rev Neurother. 2011 May; 11(5): 665-676). Individuals with mild cognitive impairment exhibiting a higher level of Parkinsonism have a higher risk of the subsequent development of Alzheimer disease (see Buracchio T, Dodge H H, Howieson D, Wasserman D, Kaye J. The trajectory of gait speed preceding mild cognitive impairment. Arch. Neurol. 2010; 67(8):980-989; Camicioli R, Howieson D, Oken B, Sexton G, Kaye J. Motor slowing precedes cognitive impairment in the oldest old. Neurology. 1998; 50(5):1496-1498.). A higher level of parkinsonian signs prior to the diagnosis of Alzheimer disease is associated with a more rapid rate of cognitive decline both before and after the diagnosis of Alzheimer disease (see Portet F, Scarmeas N, Cosentino S, Helzner E P, Stern Y. Extrapyramidal signs before and after diagnosis of incident Alzheimer disease in a prospective population study. Arch. Neurol. 2009; 66(9):1120-1126; Wilson R S, Schneider J A, Bienias J L, Evans D A, Bennett D A. Parkinsonianlike signs and risk of incident Alzheimer disease in older persons. Arch. Neurol. 2003; 60(4):539-544).

In the method consistent with the current invention, detecting anomaly (step of 208) in a subject's power spectra and making diagnosis (step of 210) of brain injuries may include comparing the subject's power spectra against a database of spectra obtained from patients with brain injuries. In an exemplary embodiment, power spectra are examined over the entire frequency spread in which signal strength or amplitude of each frequency (Hz) is analysed for difference between the subject and an age-matched dataset. In another exemplary embodiment, the differences of signal strength or energy in discrete frequency bandwidths and energy ratios of one frequency bandwidth(s) over other frequency bandwidth(s) are computed and used to make diagnosis of mTBI and severity of brain injuries.

In an exemplary embodiment of this invention, the method of making diagnosis based on anomaly of EMG power spectra associated with brain injury and neurodegenerative diseases include quantifying changes in prokinetic regions of the frequency power spectra and those in the anti-kinetic regions. The method, according to the current invention, further includes quantifying the ratios of signal strength or energy in different bandwidths and the ratios of the energy in prokinetic bandwidths over the energy in anti-kinetic bandwidths. These changes in prokinetic and anti-kinetic bandwidths, as well as other changes in EMG power spectra, reflect both functional impairment and structural damage in the cortical and subcortical network concerned with motor modulation. They also serve as a quantifiable proxy for a broad spectrum of signs and symptoms associated with brain injury and dysfunction. Consistent with the current invention, the aberrant neurological modulation of motor activity reflected in EMG power spectra are associated with brain functional disturbance and structural damage. In accordance with the current invention, the quantitative features in the altered EMG power spectra is used to judge the severity of brain dysfunction and injury as well as making prognosis and treatment suggestion. Even among young population of university students, our testing with the method, in accordance with the current invention, shows that the concussed individuals borne the telltale markers of depressed prokinetic signal strength as well as increased anti-kinetic signal strength in their EMG power spectra. These quantitative markers can be used to correlate with the numbers and severity of a subject's concussion as well as recovery from previous concussions. The method also detected altered EMG power spectra in an ice hockey player who had no concussion history but was believed to have repetitive sub-concussive episodes while playing competitive ice hockey.

Consistent with the method in the current invention, making diagnosis include impaired neurological modulation of motor activity associated with chronic traumatic encephalopathy, Alzheimer disease and Parkinson's disease. Severe or repetitive mTBI produce a broad spectrum of neurodegenerative diseases that impair motor control. The method, in accordance with the invention, makes diagnosis and differential diagnosis based on impaired neurological modulation of motor activity identified in the subject's EMG spectra in combination with the examination of patient's history and disease etiology. Consistent with the method, the increase in the anti-kinetic bandwidths including the region centered around 30 Hz are pronounced in Parkinsonian disorders. In an exemplary embodiment, diagnosis of Parkinson's disease is made in reference of the patient's EMG power spectra, history, and classic Parkinsonian signs and symptoms (rest tremor, akinesia, and rigidity). The method further provides monitoring and evaluating drug effect and other therapeutic treatment by acquiring consecutive EMG power spectra over the course of the treatment. The method further enables objective evaluation of treatment efficacy, disease progression, and recovery based on numeric values derived from quantitative features of the EMG power spectra of patients with mTBI and neurodegenerative diseases.

In an exemplary embodiment of the method, diagnosing neurodegenerative diseases include early diagnosis of Alzheimer disease. Alzheimer disease can be a consequence of severe or repetitive mTBI. Although most cases of Alzheimer disease do not have history of brain injury, the aspect of balance impairment and progressive motor decline in Alzheimer precede cognitive decline by several years in preclinical Alzheimer patients. It has been increasingly recognised that early diagnosis benefits treatment and delays the progression of Alzheimer disease. It is further recognized that assessment of balance and postural control provide promising detection and risk assessment of Alzheimer disease over the traditional cognitive evaluation which tends to be variable and influenced by test condition (see "Sensory and Motor Dysfunction in Aging and Alzheimer's Disease" on National Institute on Aging webpage https://www.nia.nih.gov/about/events/2011/sensory-and-motor-dysfunction-aging-and-alzheimers-disease#sthash.NYZiY6lm.dpuf). The method described in the current invention offers an entirely novel assessment of neurological modulation of motor activity for screening and risk detection of Alzheimer disease. The method future provides Alzheimer disease diagnosis based on comprehensive evaluation of the subject's EMG power spectra, risk factors, and cognitive assessment.

In a preferred embodiment of the invention, the method for the assessment of impaired neurological modulation of motor control associated with mTBI and neurodegenerative diseases is embedded in the device 100 that comprises EMG sensor device 104, an analog electronics module 106, an digital control block 118, an interactive display screen 108, and rechargeable battery 112.

Referring to FIG. 1, an analog electronics module 106 may perform amplification, filtering, and preprocessing of the analog EMG signals acquired by the EMG sensor device 104. The analog electronics module also contains an analog-to-digital converter (ADC). The digital data can then be passed to and processed by the digital processing block 118.

Digital processing block 118 includes a processor 120 and a memory unit 122. Referring to FIG. 1, the digital processing block 118 may also be operatively connected to several components or devices. The memory 122 stores the operational instructions for administering the tests and for data processing such as a digital signal processing algorithm. In an exemplary embodiment, the digital processor 120 can be configured to perform the following tasks:
1. Transforming the acquired data from the analogy electronics module into frequency power spectra by applying Fourier transformation algorithm such as discrete Fourier transformation or other variants of Fourier transformation family of algorithm;
2. Analysing the resultant power spectra in which the power in each frequency (Hz) is expressed as the percentage of total spectral power over the entire frequency range;
3. Extracting non-linear and linear features of the processed signals;
4. Comparing quantitative features of the subject's EMG frequency power spectra against those in databases presenting age-normalized control group and groups with brain injury and neurodegenerative diseases.

The digital processing block 118 is configured to execute instructions and algorithm installed in memory 122 to extract quantitative features from acquired EMG signals. The algorithm extracts various linear and non-linear features from the power spectra. In exemplary embodiments, the features computed include, but are not limited to, total power in the entire frequency range, relative power for each frequency, average and mean powers in frequency bandwidths, ratios of powers in one bandwidth over another bandwidth, statistical harmonics variables, Wavelet features, fractal dimension, coherence, and symmetry. Furthermore, in an embodiment consistent with the current invention, the processor 120 is configured to compare the subject's numerical values of quantitative features with corresponding normative values of ag-matched control group and/or with those indicative of brain injuries and brain dysfunctions.

In an exemplary embodiment, software in the memory 122 runs instructions and procedures of testing. The software can be configured to display a main menu and sub-menus on a display screen 108. The menu may include user tutorial and step-by-step operation procedure. The procedure provides guide to complete various tests under different conditions pertaining to where and how muscle EMG signals are recorded on the body such as muscle names, side of body being tested, and eye open or eye closed during a test. The memory 122 can further be configured to allow a user to add subject specific information about each test via the interactive display screen 108.

The plurality of tests during which EMG signals are collected from different sites of the body, muscles, and with eye open or closed will furnish data that enable making determinations including possible brain injury location, affected brain functions, and severity.

In accordance with the current invention, the diagnostic determinations as well as numeric values of quantitative features and their normative reference values can be displayed on the screen 108, stored in memory 122, and printed out 126. Also In an embodiment consistent with this invention, the entire data set of the subject can be transferred to a PC 124 for storage and further analysis.

Consistent with the current invention, the device further allows collection of information on the subject suspected of having a concussion based on the Standardized Concussion Assessment Tool (SCAT). SCAT is an evaluative method for concussion. This tool was developed by a group of international experts and adapted by major international sport organizations. The latest version of the SCAT, SCAT3, includes assessment of a concussed individual in categories such as Glasgow coma score, symptom evaluation, cognitive assessment, and balance examination. SCAT3 is published in British Journal of Sports Medicine 2013, Volume 47, Issue 5. The SCAT procedure can be installed in the memory 122 and conducted by a user. The results of SCAT can be recorded by the user via the interactive screen 108 and used as correlational reference to the diagnosis and quantitative features based on EMG frequency power spectra analysis disclosed in the current invention.

In an exemplary embodiment, the EMG sensor device with electrodes 104 may be wirelessly coupled to the base unit 100 that receives the acquired EMG signals. The base unit 100 further contains a touch screen as an interactive screen that allows display as well as data entry.

In summary, this disclosure describes a novel method of assessing the neurological modulation impairment of motor activity based on analysis of EMG power spectra. In accordance with the current invention, such assessment is made in order to make diagnosis of mTBI and neurodegenerative diseases that include chronic traumatic encephalopathy, dementia, Alzheimer disease, and Parkinsonian disorder. These conditions share extensive overlapping pathology, motor-related dysfunction, and certain risk factors. Impairment or irregularity of neurological motor control is the most common and early finding among the signs and symptoms of these conditions. Consistent with this invention, the disclosure of the current invention includes EMG frequency power spectra analysis and significant changes in unique bandwidths in prokinetic and anti-kinetic frequency regions as well as other changes. Such changes are not only of diagnostic value but also provide mechanistic insight of the motor behavior abnormality associated with brain injury and neurodegenerative diseases. Consistent with this invention, the method further provides a diagnostic strategy that holds several advantages over the prior art and offers new objective numerical evaluation that amends the deficiency of the prior art in diagnosing and monitoring mTBI, chronic traumatic encephalopathy, Parkinsonian disorder, and Alzheimer disease. The application of the method and device are broad and important.

The invention claimed is:

1. A method for testing a subject for a brain condition comprising at least one of mild traumatic brain injury (mTBI), Alzheimer's disease, Parkinson's disease, and chronic traumatic encephalopathy using a portable device, the method comprising:

acquiring, by a processor, electromyogram (EMG) signals of the subject from a detection area of the body using an EMG sensor device operatively coupled to a portable base unit, wherein the detection area of the body includes an area of muscles that are active while the subject is engaging in a physical task and the EMG signals are acquired while the subject engages in the physical task, the physical task comprising at least one of a walking gait cycle and a balance test;

processing, by the processor, the acquired EMG signals using the processor of the base unit and software to transform the EMG signals into EMG power spectra data, wherein the EMG power spectra data is characterized by a frequency spread, and determining quantitative features of the EMG power spectra data using at least one of linear and non-linear algorithms, wherein determining quantitative features comprises determining at least a ratio of a first energy value and a second energy value where the first energy value is obtained from a first frequency range in the EMG power spectra data and the second energy value is obtained from a second frequency range in the EMG power spectra data, wherein each of the first frequency range and the second frequency range comprises at least one of: (a) approximately 30 Hz, (b) approximately 35 Hz to 70 Hz, (c) approximately 74 Hz to 75 Hz, (d) approximately 79 Hz to 80 Hz (e) approximately 93 Hz to 95 Hz, (f) approximately 60 Hz to 150 Hz, and (g) approximately 160 Hz to 320 Hz, and wherein the first frequency range is different than the second frequency range;

comparing, by the processor, the subject's EMG power spectra data and the determined quantitative features against those in at least one database;

determining, by the processor, when the subject has at least one of mild traumatic brain injury (mTBI), Alzheimer's disease, Parkinson's disease and chronic traumatic encephalopathy based on the comparisons;

generating, by the processor, diagnostic information based on the comparison and determination, wherein the diagnostic information comprises at least one of the presence, location, and severity of a brain injury and the quantitative features of the subject; and displaying, on an interactive screen, at least one of the diagnostic information and the quantitative features.

2. The method according to claim 1, wherein acquiring the EMG signals of the subject includes recording the EMG signals in an area over muscles of the subject that are undergoing sustained contraction at submaximal or maximal level while the subject's eyes are open or closed.

3. The method according to claim 1, wherein acquiring the EMG signals of the subject includes recording the EMG signals while the subject is standing on one leg on a flat or tilted surface and maintaining balance without assistance or with assistance while the subject's eyes are open and while the subject's eyes are closed.

4. The method according to claim 1, wherein acquiring the EMG signals of the subject includes collecting the EMG signals in areas over muscles in the subject's extremities, waist, and trunk or over the subject's peroneus longus muscle.

5. The method according to claim 1, wherein acquiring the EMG signals of the subject includes recording the EMG signals on muscles from at least one of both limbs and both sides of the subject's body.

6. The method according to claim 1, wherein processing the acquired EMG signals includes transforming the acquired EMG signals into the frequency domain to obtain the EMG power spectra data by using at least one frequency transformation algorithm comprising a discrete Fourier transform (DFT), a fast Fourier transformation (FFT), or a Wavelet transformation.

7. The method according to claim 6, wherein the frequency spread of the EMG power spectra is at least 500 Hz, and the quantitative features comprise at least one of computed total power in discrete frequency bandwidths relative power.

8. The method according to claim 1, wherein comparing the quantitative features and the EMG power spectra data of the subject includes comparing the subject's quantitative features and the EMG power spectra data with comparison data from a database comprising normative data indicative of normal EMG power spectra data for subjects without brain injuries to determine when the subject has at least one of mild traumatic brain injury (mTBI), Alzheimer's disease, Parkinson's disease and chronic traumatic encephalopathy based on differences between the subject's quantitative features and EMG power spectra data and normal EMG power spectra data and quantitative features for subjects without brain injuries in the database.

9. The method according to claim 8, wherein determining when the subject has at least one of mild traumatic brain injury (mTBI), Alzheimer's disease, Parkinson's disease and chronic traumatic encephalopathy further comprises determining an additional quantitative feature comprising when there are signal-strength changes within a prokinetic frequency range which is the second frequency range of about 60-150 Hz of the subject's EMG power spectra data based on comparison with the prokinetic frequency range of normal EMG power spectra data associated with subjects without brain injuries in the database.

10. The method according to claim 8, wherein determining when the subject has at least one of mild traumatic brain injury (mTBI), Alzheimer's disease, Parkinson's disease and chronic traumatic encephalopathy further comprises determining an additional quantitative feature comprising when there is reduced signal-strength in the range of at least one of approximately 35-70 Hz, approximately 74-75 Hz, approximately 79-80 Hz, and approximately 93-95 Hz of the subject's EMG power spectra data based on comparison with the same ranges in normal EMG power spectra data associated with subjects without brain injuries in the database.

11. The method according to claim 8, wherein determining when the subject has at least one of mild traumatic brain injury (mTBI), Alzheimer's disease, Parkinson's disease and chronic traumatic encephalopathy further comprises determining an additional quantitative feature comprising when there are signal-strength changes in an additional frequency range comprising an antikinetic frequency range that is less than 40 Hz of the subject's EMG power spectra data based on comparison with the antikinetic frequency range in normal EMG power spectra data associated with subjects without brain injuries in the database.

12. The method according to claim 8, wherein determining when the subject has at least one of mild traumatic brain injury (mTBI), Alzheimer's disease, Parkinson's disease and chronic traumatic encephalopathy further comprises determining when there are increased signal strength changes in an additional frequency range comprising frequency bandwidths centered around 30 Hz and 160 to 320 Hz of the subject's EMG power spectra data based on comparison with the bandwidths centered around 30 Hz and 160 to 320 Hz in normal EMG power spectra data associated with subjects without brain injuries in the database.

13. The method according to claim 1, wherein comparing the EMG power spectra data and the quantitative features of the subject against those in the at least one database includes using comparison data comprised of pre-injury test data on the subject and later test results on the subject or using the subject's tests recorded over a time period since a brain injury in order to monitor the recovery process.

14. The method according to claim 1, wherein comparing the EMG power spectra data and the quantitative features of the subject's EMG signals includes comparing EMG power spectra data collected from one limb or one side of the subject's body against the EMG power spectra data obtained from a contralateral limb or an opposite side of the subject's body and using the comparison to diagnose a brain hemisphere specific pathology.

15. The method according to claim 1, wherein determining if the subject has at least one of mild traumatic brain injury (mTBI), Alzheimer's disease, Parkinson's disease and chronic traumatic encephalopathy includes determining when the subject's EMG power spectra data corresponds to the EMG power spectra data in a database with subjects with at least one of mild traumatic brain injury (mTBI), Alzheimer's disease, Parkinson's disease and chronic traumatic encephalopathy.

16. A portable device for diagnosing at least one of mild traumatic brain injury (mTBI), Alzheimer's disease, Parkinson's disease, and chronic traumatic encephalopathy in a subject, wherein the portable device comprises:
an electromyogram (EMG) signal sensor device for acquiring EMG signals from a detection area of the body of the subject, wherein the detection area of the body includes an area of muscles that are active while the subject is engaging in a physical task and the EMG signals are acquired while the subject engages in the physical task, the physical task comprising at least one of a walking gait cycle and a balance test;
a portable base unit operatively coupled to the EMG signal sensor device comprising:
a memory unit comprising:
software having instructions for performing the assessment of neuromuscular control of the subject;
at least one database; and
a processor coupled to the memory unit, the processor being configured to:
process the acquired EMG signals to transform the EMG signals into a EMG power spectra data, wherein the EMG power spectra data is characterized by a frequency spread;
determine quantitative features from the EMG power spectra data, wherein determining quantitative features of the EMG power spectra data comprises determining at least a ratio of a first energy value and a second energy value where the first energy value is obtained from a first frequency range in the EMG power spectra data and the second energy value is obtained from a second frequency range in the EMG power spectra data, wherein each of the first frequency range and the second frequency range comprises at least one of: (a) approximately 30 Hz, (b) approximately 35 Hz to 70 Hz, (c) approximately 74 Hz to 75 Hz, (d) approximately 79 Hz to 80 Hz, (e) approximately 93 Hz to 95 Hz, (f) approximately 60 Hz to 150 Hz and (g) approximately 160 Hz to 320 Hz, and wherein the first frequency range is different than the second frequency range;
compare the subject's EMG power spectra data and the determined quantitative features with EMG power spectra data and quantitative features from the at least one database;
determine when the subject has at least one of mild traumatic brain injury (mTBI), Alzheimer's disease, Parkinson's disease, and chronic traumatic encephalopathy based on the comparison;
generate diagnostic information based on the comparison and determination, wherein the diagnostic information comprises at least one of the presence, location and severity of the brain injury and the quantitative features of the subject; and
an interactive screen that is configured to display at least one of the diagnostic information and the quantitative features.

17. The portable device according to claim 16, wherein the software further comprises instructions for receiving input of identification data for the subject, injury history for the subject, and information pertaining to a Standardized Concussion Assessment Tool (SCAT).

18. The portable device according to claim 16, wherein the at least one database comprises at least one of a normative database and a brain pathological specific database.

19. The portable device according to claim 16, wherein the processor is configured to transform the acquired EMG signals into EMG power spectra data using one of a Fourier Transform, a discrete Fourier transform (DFT), a fast Fourier transformation (FFT), and a Wavelet transformation; and extract the quantitative features from the EMG power spectra data.

20. The portable device according to claim 19, wherein energy in each frequency in the EMG power spectra data is expressed as a percentage of total power of the EMG power spectra data and the frequency spread of the EMG power spectra data spans at least from 0 to about 500 Hz.

21. The portable device according to claim 16, wherein the at least one database comprises EMG power spectra data and quantitative features from at least one preinjury test data of the subject and baseline data of individuals of comparable age and gender relative to the subject.

22. The portable device according to claim 16, wherein the at least one database comprises EMG power spectra data and quantitative features from at least one post injury test of the subject for evaluation of recovery from mTBI.

23. A non-transitory computer readable medium comprising a plurality of instructions that are executable on a processor of a portable device for adapting the portable device to implement a method for diagnosing at least one of mild traumatic brain injury (mTBI), Alzheimer's disease, Parkinson's disease, and chronic traumatic encephalopathy in a subject, wherein the method comprises:
  acquiring electromyogram (EMG) signals of the subject from a detection area of the body using an EMG sensor device operatively coupled to a portable base unit, wherein the detection area of the body includes an area of muscles that are active while the subject is engaging in a physical task and the EMG signals are acquired while the subject engages in the physical task, the physical task comprising at least one of a walking gait cycle and a balance test;
  processing the acquired EMG signals using the processor of the base unit and software to transform the EMG signals into EMG power spectra data, wherein the EMG power spectra data is characterized by a frequency spread, and determining quantitative features from the transformed EMG signals using at least one of linear and non-linear algorithms, wherein determining quantitative features comprises determining at least a ratio of a first energy value and a second energy value where the first energy value is obtained from a first frequency range in the EMG power spectra data and the second energy value is obtained from a second frequency range in the EMG power spectra data, wherein each of the first frequency range and the second frequency range comprises at least one of: (a) approximately 30 Hz, (b) approximately 35 Hz to 70 Hz, (c) approximately 74 Hz to 75 Hz, (d) approximately 79 Hz to 80 Hz (e) approximately 93 Hz to 95 Hz, (f) approximately 60 Hz to 150 Hz, and (g) approximately 160 Hz to 320 Hz, and wherein the first frequency range is different than the second frequency range;
  comparing the subject's EMG power spectra data and the determined quantitative features against those in at least one database;
  determining if the subject has at least one of mild traumatic brain injury (mTBI), Alzheimer's disease, Parkinson's disease, and chronic traumatic encephalopathy based on the comparison;
  generating diagnostic information based on the comparison and determination, wherein the diagnostic information comprises at least one of the presence, location and severity of the brain injury and the quantitative features of the subject; and
  displaying, on an interactive screen, at least one of the diagnostic information and the quantitative features.

24. The method of claim 1, wherein the method further comprises monitoring and evaluate at least one of treatment efficacy, disease progression and recovery of the subject's brain condition based on the testing determined from the subject's EMG power spectra data.

25. The portable device of claim 16, wherein the processor is further configured to monitor evaluate at least one of treatment efficacy, disease progression and recovery of the subject's brain condition based on the testing determined from the subject's EMG power spectra data.

26. The non-transitory computer readable medium of claim 23, wherein the method further comprises monitoring and evaluate at least one of treatment efficacy, disease progression and recovery of the subject's brain condition based on the testing determined from the subject's EMG power spectra data.

* * * * *